Figure 1:
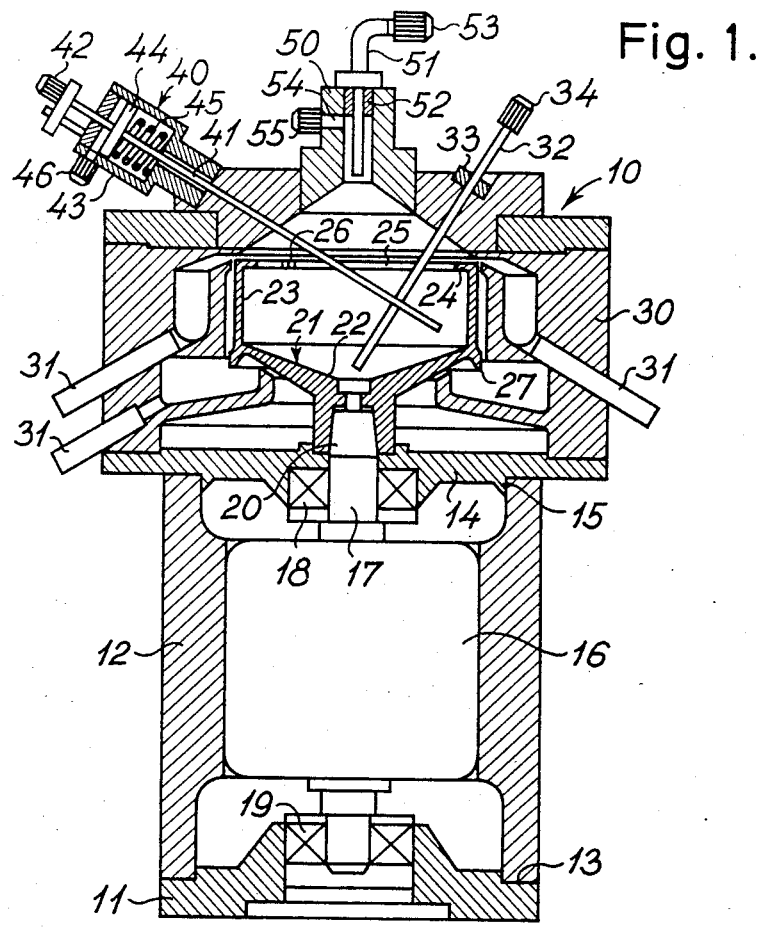

United States Patent [19]

Spinell et al.

[11] Patent Number: 4,591,445
[45] Date of Patent: May 27, 1986

[54] METHOD FOR SEPARATING BACTERIA FROM A BACTERIA CONTAINING LIQUID SAMPLE

[75] Inventors: Max Spinell, Hillerød; Bertil Engstrom, Graested, both of Denmark

[73] Assignee: N. Foss ApS, Hillerod, Denmark

[21] Appl. No.: 618,517

[22] Filed: Jun. 8, 1984

[30] Foreign Application Priority Data

Jun. 10, 1983 [DK] Denmark ............................ 2682/83

[51] Int. Cl.$^4$ ............................................. B01D 21/26
[52] U.S. Cl. .................................. 210/781; 210/782; 210/927; 422/101
[58] Field of Search ............... 210/781, 782, 787, 927; 422/101

[56] References Cited

U.S. PATENT DOCUMENTS

| | | | |
|---|---|---|---|
| 3,897,961 | 10/1976 | Sinn et al. ........................ | 210/927 X |
| 4,190,530 | 2/1980 | Forsythe, Jr. et al. ......... | 210/787 X |
| 4,322,298 | 3/1982 | Persidsky ........................ | 210/787 |
| 4,343,709 | 8/1982 | Okumura ........................ | 210/927 X |
| 4,416,778 | 11/1983 | Rogers ........................... | 210/927 X |

*Primary Examiner*—Thomas Wyse
*Attorney, Agent, or Firm*—Dennison, Meserole, Pollack & Scheiner

[57] ABSTRACT

In a method of separating bacteria from a bacteria containing liquid sample by means of a dish-like centrifuge container (21) having an upper opening (25) defined by a radially inwardly extending rim portion (24), the following sequential steps are carried out. The centrifuge container is rotated at a high rotational speed. A volume of a high density component of a density higher than the density of the bacteria is introduced into the centrifuge container, whereupon a volume of a low density component having a density lower than the density of the bacteria is introduced into the container so that a two component gradient separation layer (60) comprising a high density layer (61) and a low density layer (62) is formed within the centrifuge container (21). The liquid sample is introduced through a supply tube (32) into the center of the centrifuge container, and owing to the centrifugal force generated by the rotation of the centrifuge container, the liquid is thrown outwardly from the center of the centrifuge container. The bacteria are forced into the low density component layer (62) and deposited in the interface (63) between the two layers (61) and (62), while the liquid sample is discharged (66) from the upper opening of the centrifuge container through a notch (26). A flushing agent is introduced into the centrifuge container and discharged from the upper opening thereof together with any material adhering at the peripheral surface of the gradient separation layer (60). The centrifuge container (21) is decelerated to a low rotational speed, whereafter a suction pipette (40) is activated and moved from a first position having its tip remote from the inner surface of the peripheral wall of the centrifuge container (21) to a second position having its tip arranged adjacent to said inner surface, while a volume of a transfer liquid is introduced into the centrifuge container so that liquid substance included in the centrifuge container is sucked off therefrom through the pipette tube (41) of the suction pipette (40).

9 Claims, 2 Drawing Figures

U.S. Patent   May 27, 1986   4,591,445

METHOD FOR SEPARATING BACTERIA FROM A BACTERIA CONTAINING LIQUID SAMPLE

The present invention relates to a method of separating bacteria from a bacteria containing liquid sample. More specifically, the present invention relates to a method of separating bacteria from a bacteria containing liquid in accordance with the gradient separation principles known per se.

In many different cases, it is desirable to be able to separate bacteria from a bacteria containing liquid sample in that the bacteria content of the sample may be determined after having separated the bacteria from the sample by simply counting the number of bacteria separated from the sample in an optical measuring apparatus known per se. The liquid sample may have any organic orgin. Thus, the sample may be a blood sample or urine sample, or a suspension or solution of a solid sample, e.g. an aqueous solution or an alcoholic suspension of an organic component, e.g. a tissue or food-stuff sample. A very important example of a bacteria containing liquid sample is a milk sample. As will be appreciated, the measurement of the bacteria content of the original liquid sample is basically determined by the exactitude of the separation of the bacteria from the liquid sample. Consequently, it is of the utmost importance to be able to carry out an exact and highly accurate separation process in which bacteria exclusively are separated from the liquid sample while other particles, e.g. fat globules, blood cells or the like are not separated from the liquid sample.

It is therefore an object of the present invention to provide a method of the above kind in which it is rendered possible to carry out an exact and highly accurate separation of bacteria from a bacteria containing liquid sample excluding other particles from being separated from the liquid sample.

A further object of the present invention is to provide a method which renders it possible to carry out the separation automatically and at a high speed.

In accordance with the present invention a method of separating bacteria from a bacteria containing liquid sample by means of a dishlike centrifuge container having an upper opening defined by a radially inwardly extending rim portion is provided, comprising the following sequential steps:

(a) rotating the centrifuge container at a a high rotational speed,
(b) introducing a volume of a high density component of a density higher than the density of the bacteria into the centrifuge container,
(c) introducing a volume of a low density component of a density lower than the density of the bacteria into the centrifuge container, so as to form a two component gradient separation layer within the centrifuge container,
(d) introducing a continuous flow of the liquid sample of a density lower than the density of the low density component into the centrifuge container, whereby the bacteria are deposited in the interface between the high and the low density components of the two component gradient separation layer, while the liquid sample is discharged through the upper opening of the centrifuge container,
(e) introducing a flushing agent into the centrifuge container, whereby the flushing agent is discharged from the upper opening of the centrifuge container,
(f) decellerating the centrifuge container and rotating it at a low rotational speed,
(g) activating and moving a suction pipette from a first position having its tip remote from the inner surface of the peripheral wall of the centrifuge container to a second position having its tip arranged adjacent to said inner surface, so as to suck liquid substance from the centrifuge container, while introducing a volume of a transfer liquid into the centrifuge container without discharging transfer liquid through the upper opening of the centrifuge container, and
(h) returning the suction pipette to its first position.

In accordance with the present invention, the high density and the low density components of the two component gradient separation layer are introduced one after another in the centrifuge container while rotating the centrifuge container by means of a two speed motor at its high rotational speed. The liquid sample is introduced in a continuous flow and, consequently, the method of separating bacteria from the bacteria containing liquid sample may in principle be performed in a continuous separation process. By the introduction of the flushing agent into the centrifuge container after the carrying out of the separation process itself, any material adhering to the two component gradient separation layer, e.g. fat globules or the like, are flushed off and discharged from the upper opening of the centrifuge container. The removal of the two component gradient separation layer including the bacteria separated from the original liquid sample is carried out in accordance with the present invention by means of a suction pipette which is movable from a first position to a second position having its tip extending into the centrifuge container while rinsing the centrifuge container by means of the transfer liquid.

In accordance with a preferred embodiment of the present invention, the method further comprises the following sequential steps succeeding the steps (a)-(h):

(i) introducing a small volume of the transfer liquid into the centrifuge container without discharging liquid through the upper opening of the centrifuge container,
(j) accellerating the centrifuge container and rotating it at its high rotational speed, and
(k) repeating the steps (f)-(h).

By introducing a further volume of said liquid into the centrifuge container and accelerating the centrifuge container to its high rotational speed, any material, i.e. any component of the two component gradient separation layer or any bacteria included therein is rinsed off the centrifuge container, and consequently when repeating the steps (f)-(h) transferred to the measuring container.

In order to completely rinse the centrifuge container it is preferred to carry out the following further sequential steps succeeding the steps (a)-(k):

(l) accelerating the centrifuge container and rotating it at its high rotational speed,
(m) intermittently introducing a flow of a flushing agent and heated air into the centrifuge container in a spray, so as to rinse off any material adhering to the centrifuge container,
(n) decelerating the centrifuge container and rotating it at its low rotational speed,
(o) activating and moving the suction pipette from its first position to its second position, so as to suck any liquid substance from the centrifuge container, and
(p) returning the suction pipette to its first position.

In accordance with the present invention, the liquid may advantageously be discharged from the upper opening of the centrifuge container through a minimum width defining notch of the radially inwardly extending rim portion thereof, so as to cause a delay of the discharge of the liquid from the centrifuge container. Consequently, caused by the delay of the discharge of liquid from the centrifuge container, the liquid is maintained in the centrifuge container for a longer period of time, and consequently, the rate of supply of liquid to the centrifuge container may be increased so that a higher separation rate may be obtained.

In order to carry out the separation of bacteria from the bacteria containing liquid sample under controlled conditions, it is preferred that the method according to the invention further comprises thermostating the centrifuge container to a predetermined temperature by supplying air of said temperature to the centrifuge container. The air may be supplied in any appropriate manner, e.g. from below, so that the exterior surface of the centrifuge container is maintained at the predetermined temperature, and furthermore or alternatively, the air of the predetermined temperature may be supplied to the centrifuge container from above so that the air is introduced into the centrifuge container through the upper opening thereof.

In order to guarantee that the liquid which is discharged from the upper opening of the centrifuge container is not reintroduced into the centrifuge container caused by the suction effect generated when rotating the centrifuge container at its high rotational speed, it is preferred that a flow of pressurized air is introduced into the centrifuge container while rotating it at its high rotational speed. Preferably, the pressurized air is thermostated to the said predetermined temperature so that the flow of pressurized air further serves the purpose of thermostating the centrifuge container.

In a preferred embodiment of the invention, the high density component of the two component gradient separation layer which has a density higher than the density of the bacteria is an aqueous solution of dextran, and the low density component of the two component gradient separation layer which has a density lower than the density of the bacteria, is an aqueous solution of saccharose. The transfer liquid serving rinsing purpose when transferring the two component gradient separation layer and the bacteria included therein from the centrifuge container and also serving the purpose of rinsing off any material of the two component gradient separation layer and any bacteria included therein, may advantageously be an enzyme solution which further serves the purpose of pretreating the bacteria for the above optical counting procedure.

In the preferred embodiment of the invention, the high rotational speed of the centrifuge container is in the order of 45,000 rpm, and the low rotational speed of the centrifuge container is in the order of 250 rpm, the net volume of the centrifuge container defined therewithin when rotating the centrifuge container at its high rotational speed is in the order of 2 ml, the volume of the high density component of the two component gradient separation layer is in the order of 0.5 ml, and the volume of the low density component of the two component gradient separation layer is in the order of 1.5 ml. When rotating the centrifuge container at a rotational speed of 45,000 rpm, an extreme virtual gravitational field in the order of 50,000 G is provided in the inner space of the centrifuge container having an inner diameter in the order of 47 mm. By providing a gravitational field of such extreme intensity, a separation capacity of 1.33 ml/s is obtained, i.e. a 20 ml sample is separated within 15 s.

The present invention further relates to an apparatus for separating bacteria from a bacteria containing liquid sample in accordance with the above method comprising:

a dish-like centrifuge container having an upper opening defined by a radially inwardly extending rim portion, a two speed motor connected to the centrifuge container for selective rotation thereof at a low rotational speed and at a high rotational speed, liquid supply means extending into the centrifuge container for supply of a high density component having a density higher than the density of the bacteria to the centrifuge container, for supply of a low density component having a density lower than the density of the bacteria to the centrifuge container, for supply of a flushing agent to the centrifuge container, for supply of an enzyme solution to the centrifuge container, and for supply of the liquid sample to the centrifuge container, and a suction pipette mounted so as to be movable between a first position having its tip remote from the inner surface of the peripheral wall of the centrifuge container to a second position having its tip arranged adjacent to said inner surface, and being adapted to be activated so as to suck liquid substance from the centrifuge container.

By means of the apparatus according to the invention, it is rendered possible to carry out the separation of bacteria from a bacteria containing liquid sample in an automatized, high speed and highly accurate separation process. A particular feature of the apparatus according to the invention is the suction pipette which is mounted so as to be movable into the centrifuge container between its first and its second positions. By employing such a suction pipette, a highly reliable and exact transfer of material included in the centrifuge container is obtained without any risk of damaging the centrifuge container as the tip of the suction pipette is always kept out of contact with the inner surface of the centrifuge container.

Although the supply means may be constituted by a single means for supply of all liquids and components to the centrifuge container and may terminate in any part thereof, e.g. extend through the bottom wall of the centrifuge container, the supply means are preferably constituted by individual supply tubes extending into the centrifuge container through the upper opening thereof and for supply of the high density component, the low density component, the flushing agent, the enzyme solution, and the liquid sample, respectively.

As explained above, a flow of pressurized air is introduced into the centrifuge container while rotating it at its high rotational speed. The pressurized air is preferably also supplied from a supply tube extending into the centrifuge container through the upper opening thereof.

In accordance with a preferred embodiment of the apparatus according to the invention, the dish-like centrifuge container is further provided with a notch defining the minimum width of the radially inwardly extending rim portion thereof. Caused by the notch, a liquid reservoir is formed within the centrifuge container as the liquid is only discharged from the upper opening of the centrifuge container through the notch and, consequently, the liquid is maintained in the centrifuge container for a longer period of time.

In the preferred embodiment of the apparatus according to the invention, the dish-like centrifuge container is made of titanium and provided with an interior coating of polytetrafluoro-ethylene, the inner diameter of the centrifuge container being in the order of 47 mm and the net volume of the inner space of the centrifuge container being in the order of 2 ml. By providing the centrifuge container as a titanium centrifuge container, a highly rigid and strong but still extremely light-weight centrifuge container is provided.

An extreme virtual gradient field in the order of 50,000 G may be provided in the above centrifuge container by rotating the centrifuge container at its high rotational speed being in the order of 45,000 rpm. The low rotational speed of the centrifuge container is preferably in the order of 250 rpm. In this preferred embodiment of the invention, the two speed motor is connected directly to the centrifuge container through its shaft.

The invention will now be further described with reference to the drawing, wherein FIG. 1 is a vertical sectional view of a preferred embodiment of an apparatus for separating bacteria from a bacteria containing liquid sample, and FIG. 2 a partly sectional, diagrammatical view illustrating the general separation method according to the invention.

In FIG. 1 an apparatus for separating bacteria from a bacteria containing liquid sample, e.g. a milk sample is shown. The apparatus is designated 10 in its entirety and provided with a base 11 on which a cylindrical casing 12 is mounted. The lower end portion of the cylindrical casing 12 is secured to the base 11 and received in a cylindrical, circumferential recess thereof. On top of the cylindrical casing 12 a floor 14 is mounted. The floor 14 is secured in relation to the cylindrical casing 12 by means of a cylindrical rim projecting from the lower side surface of the floor 14. In the cylindrical casing 12 a motor 16 is encapsulated. The motor 16 is a two speed motor which is adapted to generate a high speed rotation in the order of 45,000 rpm and a low speed rotation in the order of 250 rpm. The motor 16 has its shaft 17 journalled in a top bearing 18 and a bottom bearing 19 arranged in the floor 14 and the base 11, respectively. The shaft 17 extends beyond the top bearing 18 and is provided with an inwardly tapering cone 20 at its upper end.

A dish-like centrifuge container 21 is mounted on the shaft 17 and at its lower end provided with an outwardly tapering conical recess of a tapering rate identical to the tapering rate of the inwardly tapering cone 20 of the shaft 17. Consequently, the cones of the shaft 17 and of the dish-like centrifuge container 21 secure the centrifuge container 21 in relation to the motor shaft 17. The centrifuge container 21 which is shown in greater detail in FIG. 2 and is to be described below, comprises a conical bottom portion 22, a vertical cylindrical portion 23, and an inwardly extending rim portion 24 defining an upper opening 25 of the centrifuge container 21. At the upper opening 25 of the centrifuge container 21, the inwardly extending rim portion 24 is provided with a notch 26 defining the minimum radial width of the rim portion. Furthermore, the centrifuge container 21 is provided with a downwardly projecting separating skirt 27 which serves the purpose of preventing liquid from getting into contact with the top bearing 18. In order to further prevent liquid or droplets from getting into contact with the top bearing 18, a flow of air of a predetermined temperature, further serving the purpose of thermostating the centrifuge to the predetermined temperature, is supplied to the centrifuge container from below through a supply tube, not shown on the drawings, so as to generate a separating air curtain surrounding the lower part of the centrifuge container.

On top of the floor 14, a housing 30 is arranged encapsulating the centrifuge container 21. The housing 30 is at its vertical cylindrical side wall provided with outlets 31 serving the purpose of letting out liquid from the housing 30. A supply tube 32 for supply of a liquid sample extends into the interior of the housing 30 through a bore of the housing 30, and further through the upper opening 25 of the centrifuge container 21 and into the interior thereof. The supply tube 32 is secured and sealed in relation to the housing 30 by means of a sealing ring or gasket 33 and is provided at its upper end with a connecting fitting 34 allowing connection to an appropriate tubing, not shown on the drawings. The supply tube 32 is adapted to be connected to an external liquid sample container through its connecting fitting 34 and said tubing, not shown on the drawings.

In another cylindrical bore at the top of the housing 30, a suction pipette, generally designated 40, is arranged. The suction pipette 40 comprises a pipette tube 41 which extends into the interior of the housing 30 and further through the opening 25 of the centrifuge container 21 into the interior thereof. At the upper end, the pipette tube 41 is provided with a connecting fitting 42 allowing connection to external containers, not shown on the drawings, through appropriate tubings and valves, not shown on the drawings. The suction pipette 40 further comprises a pipette housing 43 through which the pipette tube 41 extends. As is evident from FIG. 1, the pipette tube 41 is provided with a piston member 44 which is mounted displaceably within the pipette housing 43. Within the pipette housing 43, a spring 45 is also arranged, engaging the lower side surface of the piston member 44 and biassing the piston member and consequently the pipette tube 41 outwardly in relation to the interior space of the housing 30. A connecting fitting 46 provides access to the upper side surface of the piston member 44 and is adapted to be connected to an air pressurizing source, not shown on the drawings, through an appropriate tubing, not shown on the drawings. By applying pressurized air to the upper side surface of the piston member 44, the piston member 44 is forced downwards into the pipette housing 43 against the biassing force applied to the lower side surface of the piston member 44 by the spring 45 and, consequently, moves the tip of the pipette tube 41 further into the interior space of the centrifuge container 21.

At the center of the top of the housing 30, a body 50 is arranged. In a through-going bore of the body 50, a tube 51 is arranged and sealed in relation to the body 50 by means of a sealing ring or gasket 52. The upper end of the tube 51 is provided with a connecting fitting 53 allowing connection to an external fluid source, not shown on the drawings, through an appropriate tubing, not shown on the drawings. Perpendicularly to the through-going bore of the body 50, a bore 54 provides communication thereto from a connecting fitting 55. The connecting fitting 55 is adapted to be connected to an external air pressurizing source, not shown on the drawing, through an appropriate tubing, not shown on the drawings, e.g. the above mentioned pressurizing source connected to the connecting fitting 46 of the suction pipette 40. The supply of pressurized air through the connection fitting 55 and further through the through-going bore of the body 50 serves two purposes. Firstly, the air, which is maintained at a predetermined temperature, serves the purpose of thermostating the centrifuge container to the predetermined temperature. Secondly, the pressurized air serves the purpose of preventing liquid from being collected at the interior surface of the housing 30 and from being sucked into the centrifuge container when rotating the centrifuge container at its high rotational speed of 45,000 rpm.

Figure 2:
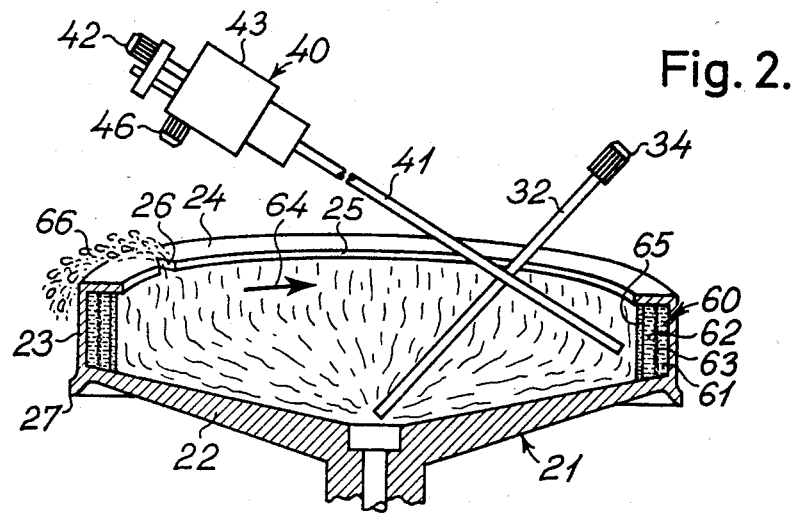

In FIG. 2 the centrifuge container 21 is shown in greater detail. While the centrifuge container 21 is rotating at its high rotational speed, driven by the motor 16 as indicated by an arrow 64, a two component gradient separation layer 60 is arranged in a circumferential inner space of the centrifuge container 21 defined by the minimum width defining notch 26 of the inwardly extending rim portion 24. The two component separation layer 60 comprises a high density component constituting a first layer 61 and a low density component constituting a second layer 62 arranged on top of the first layer 61. The high density component and the low density component of the first and the second layers 61 and 62, respectively, are of densities higher and lower, respectively, than the density of the bacteria to be separated. In the interface of the layers 61 and 62, a bacteria layer 63 is shown. The liquid sample is supplied to the center of the centrifuge container 21 through the supply tube 32 and discharged therefrom. Owing to the centrifugal force generated by rotating the centrifuge container 21 at its high rotational speed, the liquid is thrown outwardly from the center of the centrifuge container and forced upwardly along the inner surface of the layer 62. The liquid which is supplied from the supply tube 32 in a continuous flow generates a liquid film layer 65 at the inner surface of the low density component layer 62 and is discharged through the notch 26 as indicated by the reference numeral 66. As the liquid is only discharged through the notch 26, the liquid is maintained in the centrifuge container for a longer period of time when compared to a dish-like centrifuge container not having the minimum width defining notch 26 in which the liquid is discharged from the total upper opening of the centrifuge container and, consequently, the rate of supply of liquid to the centrifuge container may be increased further increasing the rate of separation of bacteria when compared to an apparatus not having the notch 26. As the bacteria are of a higher density than the low density component layer or inner layer 62, the bacteria are forced radially through the layer 62 to the interface of the layers 61 and 62.

The operation of the apparatus 10 is described in the example below.

EXAMPLE

In a practical embodiment of the kind described above with reference to the drawings, the dish-like centrifuge container 21 was made of titanium and provided with an interior polytetrafluoro-ethylene surface coating. The inner diameter of the centrifuge container 21 was 47 mm. The motor 16 was adapted to be driven at a low rotational speed of 250 rpm and a high rotational speed of 45,000 rpm providing a virtual gravitational field in the centrifuge container in the order of 50,000 G. The circumferential inner space of the centrifuge container 21, the height thereof being defined by the minimum width defining notch 26 of the inwardly extending rim portion 24, was in the order of 2 ml. In this embodiment, a 15 ml liquid sample was separated within 15 s. The 20 ml liquid sample was an aqueous solution of a 5 ml milk sample. Through the connecting fitting 55 and through the through-going bore of the body 50 a flow of pressurized air heated to a temperature of 40° C. was continuously supplied from a 1.5 Bar pressurizing source through a tubing of an interior diameter of 1.5 mm and of a length of 250 mm. As mentioned above a flow of air of a temperature of 40° C. was also supplied to the centrifuge container from below.

When carrying out the separation process according to the invention, the above apparatus according to the invention was driven in an automatized sequence comprising the following steps:

(a) the motor 16 was accelerated to its high rotational speed for rotating the centrifuge container 21 at its high rotational speed of 45,000 rpm, (b) an 0.5 ml aqueous dextran solution constituting the high density component was supplied from a separate supply tube, not shown on the drawings, to the center of the centrifuge container, whereupon the aqueous dextran solution was thrown into the circumferential inner space of the centrifuge container 21 and into the high density component layer or first layer 61 shown in FIG. 2, (c) a 1.5 ml saccharose solution constituting the low density component was supplied through a separate supply tube, not shown on the drawings, to the center of the centrifuge container, whereupon the saccharose solution was thrown into the low density component layer or second layer 62 shown in FIG. 2, while any excessive saccharose volume was discharged from the upper opening 25 of the centrifuge container 21 through the minimum width defining notch 26 of the inwardly extending rim portion 24, (d) the liquid sample was supplied from the supply tube 32 in a continuous flow so that the bacteria were deposited in the bacteria layer 63 of the interface of the first and the second layers 61 and 62, respectively, and the liquid was discharged through the upper opening 25 of the centrifuge container as indicated by the reference numeral 66 of FIG. 2, (e) thus having concluded the separation process itself, a flushing agent constituted by an enzyme solution was supplied from a separate supply tube, not shown on the drawings, to the center of the centrifuge container so that any particles, e.g. fat globules which might influence the bacteria counting process to be carried out later, were rinsed off and discharged from the centrifuge container 21, (f) the motor 16 was decelerated to its low rotational speed for rotating the centrifuge container 21 at its low rotational speed of 250 rpm, (g) the suction pipette 40 was activated and moved from a first position having its tip remote from the inner surface of the peripheral wall of the centrifuge container to a second position having its tip arranged adjacent to said inner surface as evident from FIG. 2, while a 1.5 ml volume of the enzyme solution was supplied from the above supply tube, not shown on the drawings, to the center of the centrifuge container 21 so that the material of layers 61 and 62 also including the bacteria interface deposit 63 was transferred in an enzyme solution through the pipette tube 41 and further through the connecting fitting 42 and an external tubing, not shown on the drawings, to an external measuring container or measuring equipment, not shown on the drawings, (h) the suction pipette was returned to its first position, (i) a 1.5 ml enzyme solution volume was supplied through the above supply tube, not shown on the drawings, to the center of the centrifuge container 21, (j) the motor 16 was accelerated for rotating the centrifuge container 21 at its high rotational speed of 45,000 rpm so that any material arranged within the circumferential inner space of the centrifuge container 21 was rinsed off by means of the enzyme solution volume, and (k) thereafter the steps (f)-(h) were repeated for transferring the rinsing 1.5 ml enzyme solution volume together with any material dissolved therein to the above measuring container or measuring equipment, not shown on the drawings.

For rinsing the entire apparatus, the following sequential steps were carried out:

(l) the motor 16 was accelerated for rotating the centrifuge container 21 at its high rotational speed of 45,000 rpm, (m) a flushing agent supplied through the supply tube 51 and air supplied through the bore 54 from a preheater heating the air to a temperature of approximately 40° C. were intermittently introduced into the interior space of the housing 30, the interval being in the order of 0.5 s, in a spray serving the purpose of rinsing the interior surfaces of the housing 30 and the outer surfaces of the centrifuge container 21, (n) the motor 16 was decelerated for rotating the centrifuge container at its low rotational speed of 250 rpm, (o) the suction pipette was activated and was moved from its first to its second position so that any liquid and any material present in the centrifuge container were sucked off and transferred through the pipette tube 41 and further through the connecting fitting 42 and through an external tubing, not shown on the drawings, to a waste container, and (p) finally the suction pipette was returned to its initial position, and the motor 16 was turned off.

We claim:

1. A method of separating bacteria from a bacteria containing liquid sample by means of a dish-like centrifuge container having an upper opening defined by a radially inwardly extending rim portion, comprising the following sequential steps:

(a) rotating the centrifuge container at a high rotational speed, (b) introducing a volume of a high density component of a density higher than the density of the bacteria into the centrifuge container, (c) introducing a volume of a low density component of a density lower than the density of the bacteria into the centrifuge container, so as to form a two component gradient separation layer within the centrifuge container, (d) introducing a continuous flow of the liquid sample of a density lower than the density of the low density component into the centrifuge container, whereby the bacteria are deposited in the interface between the high and the low density components of the two component gradient separation layer, while the liquid sample is discharged through the upper opening of the centrifuge container, (e) introducing a flushing agent into the centrifuge container, whereby the flushing agent is discharged from the upper opening of the centrifuge container, (f) decelerating the centrifuge container and rotating it at a low rotational speed, (g) activating and moving a suction pipette from a first position having its tip remote from the inner surface of the peripheral wall of the centrifuge container to a second position having its tip arranged adjacent to said inner surface, so as to suck liquid substance from the centrifuge container, while introducing a volume of a transfer liquid into the centrifuge container without discharging transfer liquid through the upper opening of the centrifuge container, and (h) returning the suction pipette to its first position.

2. A method according to claim 1, further comprising the following sequential steps succeeding the steps (a)-(h):

(i) introducing a small volume of the transfer liquid into the centrifuge container without discharging liquid through the upper opening of the centrifuge container, (j) accelerating the centrifuge container and rotating it at its high rotational speed, and (k) repeating the steps (f)-(h).

3. A method according to claim 2, further comprising the following sequential steps succeeding the steps (a)-(k):

(l) accelerating the centrifuge container and rotating it at its high rotational speed, (m) intermittently introducing a flow of a flushing agent and heated air into the centrifuge container in a spray, so as to rinse off any material adhering to the centrifuge container, (n) decelerating the centrifuge container and rotating it at its low rotational speed, (o) activating and moving the suction pipette from its first position to its second position, so as to suck any liquid substance from the centrifuge container, and (p) returning the suction pipette to its first position.

4. A method according to claim 1, the liquid being discharged from the upper opening of the centrifuge container through a minimum width defining notch of the radially inwardly extending rim portion thereof so as to cause a delay of the discharge of the liquid from the centrifuge container.

5. A method according to claim 1, further comprising thermostating the centrifuge container to a predetermined temperature by supplying air of said temperature to the centrifuge container.

6. A method according to claim 1, a flow of pressurized air being introduced into the centrifuge container while rotating it at its high rotational speed.

7. A method according to claim 1, the high density component of the two component gradient separation layer being an aqueous solution of dextran, the low density component of the two component gradient separation layer being an aqueous solution of saccharose, and the flushing agent and the transfer liquid being an enzyme solution.

8. A method according to claim 1, the high rotational speed of the centrifuge container being in the order of 45,000 rpm, and the low rotational speed of the centrifuge container being in the order of 250 rpm.

9. A method according to claim 1, the net volume of the centrifuge container defined therewithin when rotating the centrifuge container at its high rotational speed being in the order of 2 ml, the volume of the high density component of the two component gradient separation layer being in the order of 0.5 ml, and the volume of the low density component of the two component gradient separation layer being in the order of 1.5 ml.

* * * * *